United States Patent [19]
Fey et al.

[11] Patent Number: 5,849,749
[45] Date of Patent: Dec. 15, 1998

[54] 6-(HYDROXYMETHYL-ETHYL)PYRIDINES

[75] Inventors: Peter Fey, Wuppertal, Germany; Rolf Angerbauer, Kobe, Japan; Delf Schmidt, Wuppertal, Germany; Hilmar Bischoff, Wuppetal, Germany; Wolfgang Kanhai, Wuppertal, Germany; Martin Radtke, Erkrath, Germany; Wolfgang Karl, Odenthal, Germany

[73] Assignee: Bayer Aktiengesellschaft, Leverkusen, Germany

[21] Appl. No.: 883,695

[22] Filed: Jun. 27, 1997

[30] Foreign Application Priority Data

Jul. 8, 1996 [DE] Germany ............... 196 27 420.6

[51] Int. Cl.$^6$ ............... A61K 31/44; C07F 7/02; C07D 213/30; C07D 213/55
[52] U.S. Cl. ............. 514/277; 546/14; 546/250; 546/339; 546/342
[58] Field of Search .................. 546/339, 342, 546/14, 250; 514/277

[56] References Cited

U.S. PATENT DOCUMENTS

| | | | |
|---|---|---|---|
| 4,231,938 | 11/1980 | Monaghan et al. | 549/292 |
| 4,319,039 | 3/1982 | Albers-Schonberg | 560/256 |
| 4,925,852 | 5/1990 | Kessler et al. | 514/333 |
| 4,997,837 | 3/1991 | Chucholowski et al. | 514/256 |
| 5,006,530 | 4/1991 | Angerbauer et al. | 514/277 |
| 5,169,857 | 12/1992 | Angerbauer et al. | 514/344 |
| 5,177,080 | 1/1993 | Angerbauer et al. | 514/277 |
| 5,401,746 | 3/1995 | Angerbauer et al. | 514/277 |
| 5,409,910 | 4/1995 | Angerbauer et al. | 514/89 |
| 5,418,243 | 5/1995 | Angerbauer et al. | 514/345 |

FOREIGN PATENT DOCUMENTS

| | | |
|---|---|---|
| 325130 | 6/1989 | European Pat. Off. . |
| 491226 | 6/1992 | European Pat. Off. . |
| 603699 | 6/1994 | European Pat. Off. . |
| 4321421 | 6/1994 | Germany . |

OTHER PUBLICATIONS

Journal of Chromatography, 162 (1979), pp. 281–292.

*Primary Examiner*—Alan L. Rotman
*Attorney, Agent, or Firm*—Sprung Kramer Schaefer & Briscoe

[57] ABSTRACT

The 6-(hydroxymethyl-ethyl)pyridines are prepared by a process in which the 3-hydroxymethylpyridines which are hydroxyl-protected in the 6-position are oxidized to the 3-aldehyde, this is then converted into the corresponding oxoheptenoic acid derivative using a Wittig-Homer reaction, after this the oxo group is reduced to the hydroxyl group and then the isomers are separated by chromatography. The 6-(hydroxymethyl-ethyl)pyridines are suitable as active compounds in medicaments, in particular in medicaments having antiarteriosclerotic activity.

9 Claims, No Drawings

6-(HYDROXYMETHYL-ETHYL)PYRIDINES

The invention relates to 6-(hydroxymethyl-ethyl) pyridines, a process for their preparation and their use as medicaments, in particular as antiatherosclerotic agents.

It has been disclosed that lactone derivatives isolated from fungal cultures are inhibitors of 3-hydroxy-3-methyl-glutaryl-coenzymeA reductase (HMG-CoA reductase) [mevinolin, EP22478; U.S. Pat. No. 4,231,938].

It has additionally been disclosed that pyridine-substituted dihydroxyheptenoic acids are inhibitors of HMG-CoA reductase [EP325130; EP307342; EP306929].

It has now been found that the 6-(hydroxymethyl-ethyl) pyridines of the general formula (I)

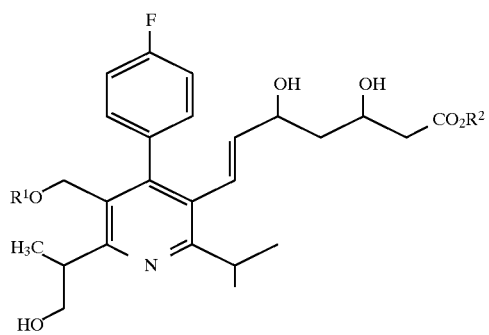

in which $R^1$ represents hydrogen or methyl, and $R^2$ represents hydrogen or methyl, and their salts, if appropriate in an isomeric form, have a superior inhibitory action on HMG-CoA reductase and thus bring about a surpringly good lowering of the cholesterol content in the blood.

The compounds according to the invention can also be present in the form of their salts. In general, salts with organic or inorganic bases may be mentioned here.

In the context of the present invention, physiologically acceptable salts are preferred. Physiologically acceptable salts of the 6-(hydroxymethyl-ethyl)pyridines according to the invention can be metal or ammonium salts. Sodium, potassium, magnesium or calcium salts may preferably be mentioned, as well as ammonium salts which are derived from ammonia or organic amines such as, for example, methylamine, ethylamine, propylamine, isopropylamine, di- or triethylamine, diisopropylamine, di- or triethanolamine, dicyclohexylamine, arginine, lysine or ethylendiamine. Sodium and potassium salts are particularly preferred.

The compounds according to the invention and their salts have 3 asymmetric carbon atoms, namely the two carbon atoms of the side chain to which the hydroxyl groups are bonded and the carbon atom to which the hydroxymethyl group is bonded.

They can therefore exist in various stereochemical forms. The invention relates both to the individual isomers and their mixtures. Depending on the relative position of the hydroxyl groups, the compounds according to the invention can be present in the erythro configuration or in the threo configuration.

The following formula scheme illustrates this by way of example:

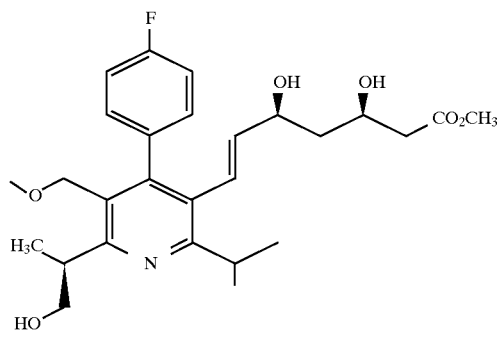

A erythro

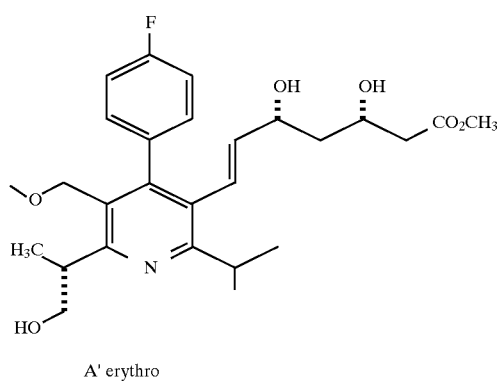

A' erythro

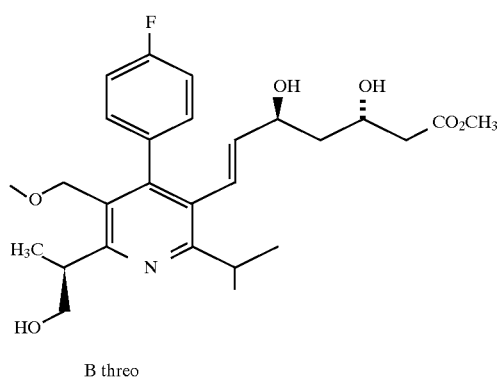

B threo

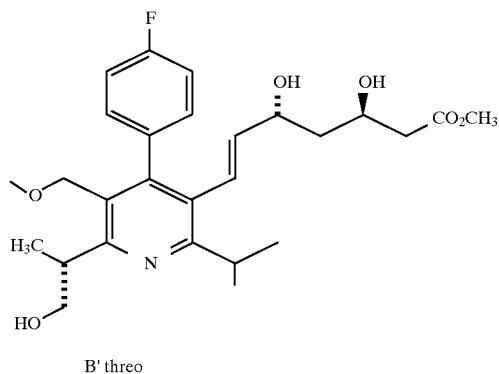

B' threo

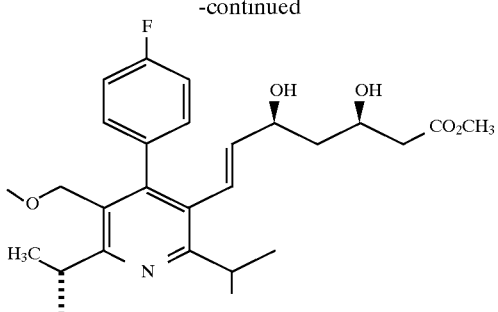

C erythro

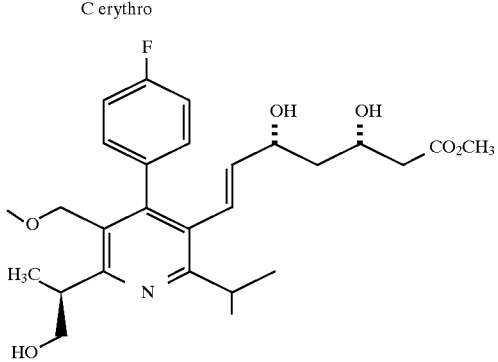

C' erythro

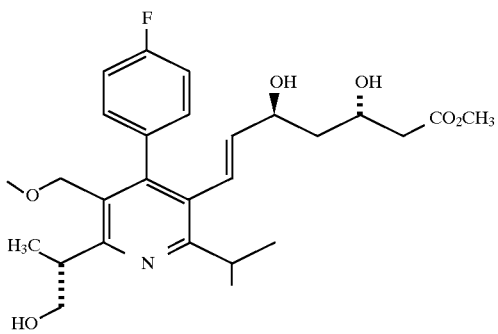

D threo

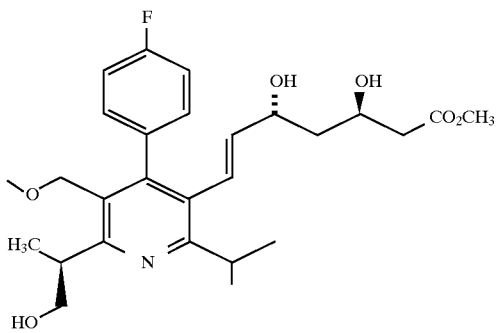

D' threo

The erythro configuration is preferred.

In turn, two enantiomers in each case exist both of the substances in the threo and in the erythro configuration, namely the 3R,5S isomer or 3S,5R isomer (erythro form) and 3R,5R isomer and 3S,5S isomer (threo form). Of these, the 3R,5S/3S,5R racemates and the 3R,5S enantiomers are preferred.

Moreover, the substances according to the invention can be present in the E configuration or the Z configuration on account of the double bond. Those compounds which have the E configuration are preferred. The 1S and 1R enantiomers of the (3R,5S)-dihydroxyheptenoic acids and derivatives in the erythro (E) configuration, and their salts are particularly preferred.

The sodium salts of the compounds according to the invention having the erythro configuration are very particularly preferred.

The compounds of the general formula (I) according to the invention can be prepared by a process in which compounds of the general formula (II)

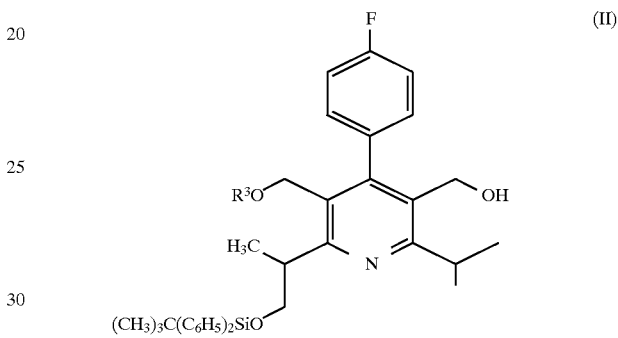

(II)

in which $R^3$ represents methyl or the radical $-Si(CH_3)_2C(CH_3)_3$ (TBDMS), are first oxidized with aluminium oxide and pyridinium chlorochromate in inert solvents to give the aldehydes of the general formula (III)

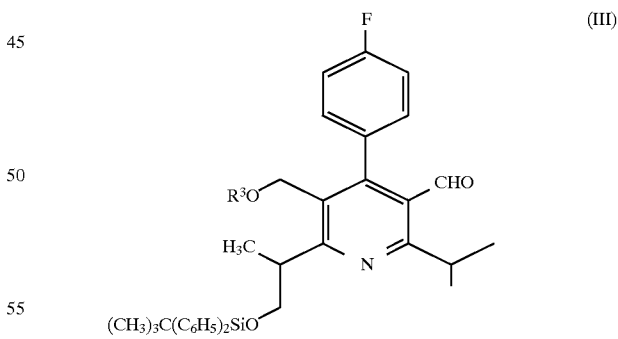

(III)

in which $R^3$ has the meaning indicated above, from these in a second step by reaction with the ketophosphonate $(CH_3O)_2PO-CH_2-CO-CH_2-CH(OSi(CH_3)_2)$ $C(CH_3)_3)-CH_2-CO_2CH_3$ in the presence of bases and solvents the compounds of the general formula (IV)

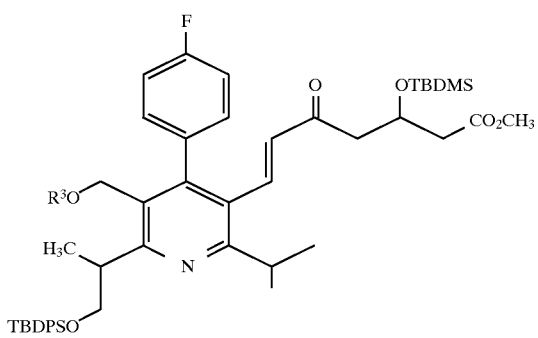

in which
TBDPS=$(CH_3)_3C(C_6H_5)_2Si$,
and
$R^3$ has the meaning indicated,
are prepared,
these are then converted by removal of the hydroxyl protective groups TBPS and TBDMS into the compounds of the general formula (V)

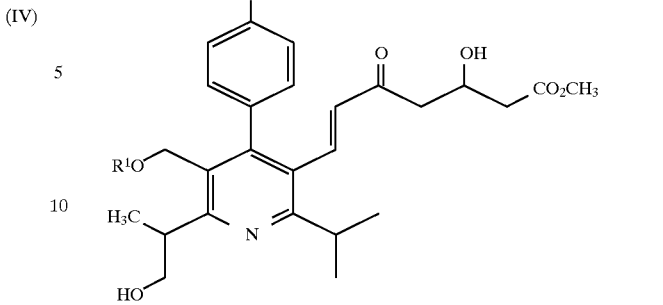

in which
$R^1$ has the meaning indicated
and in a last step the keto group is reduced in inert solvents using sodium borohydride/triethylborane,
and in the case of the acids the esters are hydrolysed,
and, if appropriate, mixtures of diastereomers are separated by chromatography or crystalization and converted into the enantiomerically pure compounds.

The process according to the invention can be illustrated by way of example by the following reaction scheme:

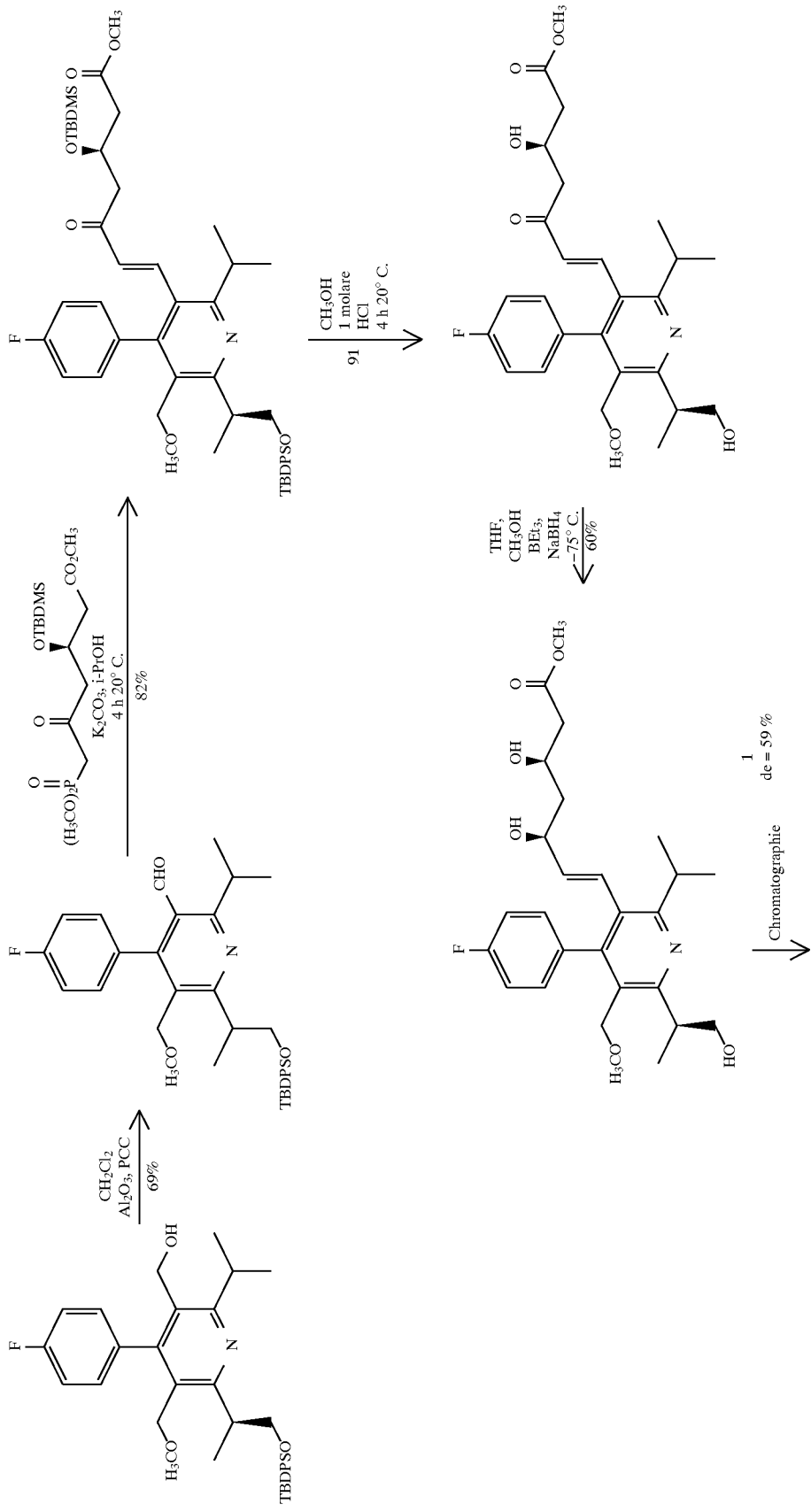

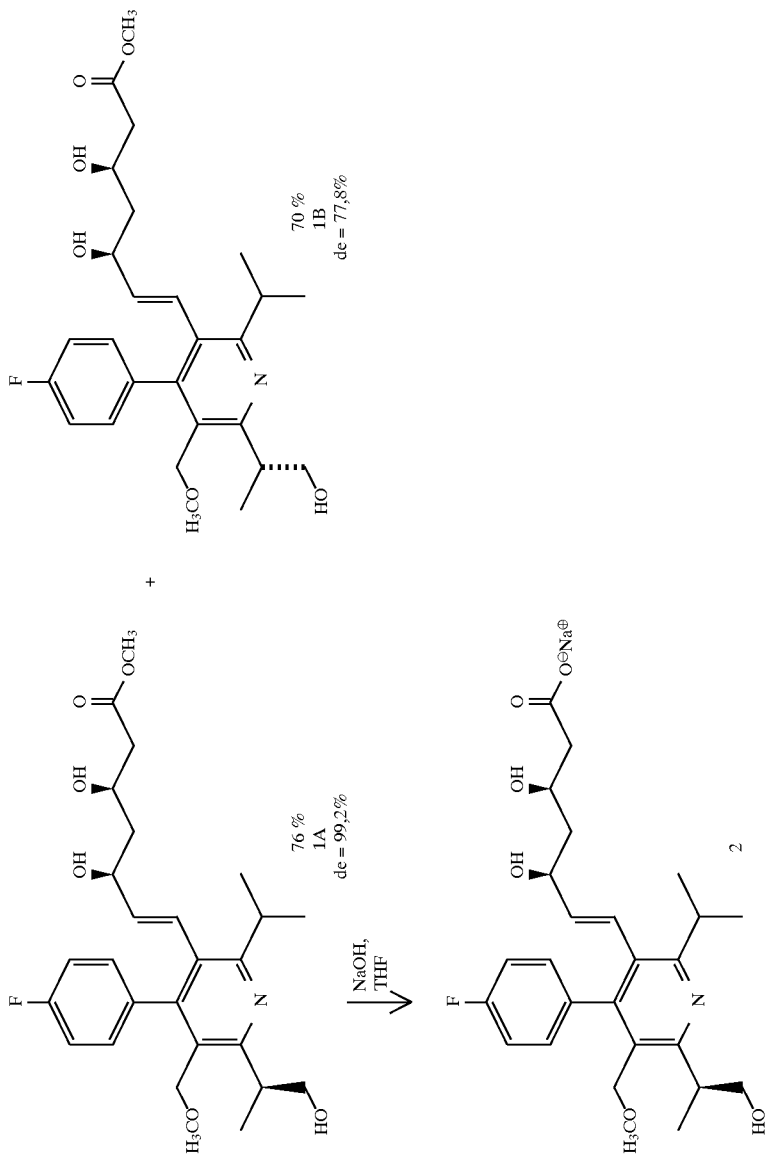

Suitable solvents for the process according to the invention are alcohols such as methanol, ethanol, propanol, ispropranol or butanol, or ethers such as tetrahydrofuran or dioxane, or dimethylformamide or dimethyl sulfoxide, halogenated hydrocarbons, such as, for example, methylene chloride or carbon tetrachloride, or water. It is also possible to employ mixtures of the solvent mentioned.

Methylene chloride is preferred for the reaction of the compounds of the general formula (II), isopropanol and water for the preparation of the compounds of the general formula (IV), and tetrahydrofuran and methanol for the reduction of the compounds of the general formula (V).

Suitable bases for the reaction of the compounds of the formula (III) are alkali metal and alkaline earth metal carbonates, potassium carbonates being preferred.

The base is employed in an amount from 0.5 mol to 5 mol, preferably from 0.8 mol to 1.2 mol, relative to 1 mol of the compounds of the general formula (III).

The removal of the hydroxyl protective groups from the compounds of the general formula (IV) is carried out using methanol and hydrochloric acid.

All reactions of the process according to the invention are carried out in a temperature range from −75° C. to +50° C., preferably at room temperature.

The reaction is in general carried out at normal pressure, but it is also possible to work at reduced pressure or elevated pressure.

The compounds of the general formula (II) are new and can be prepared by a process in which, if $R^3=CH_3$, dimethyl 6-[2-(tert-butyldiphenylsilanyloxy-1-methylethyl]-4-(4-fluorophenyl)-2-isopropyl-1,4-dihyro-pyridine-3,5-dicarboxylate of the formula (VI)

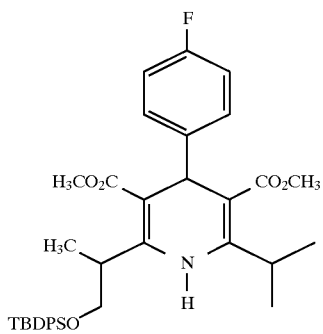

(VI)

is converted by oxidation with ammonium cerium(IV) nitrate in inert solvents into the corresponding pyridine of the formula (VII)

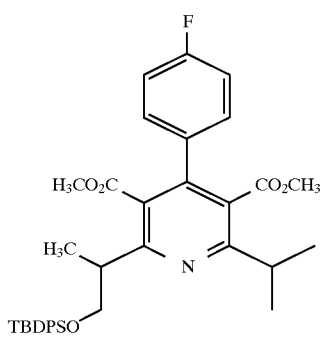

(VII)

then this is reduced under a protective gas atmosphere using diisobutyl-aluminium hydride in inert solvents to give the compounds of the general formula (VIII)

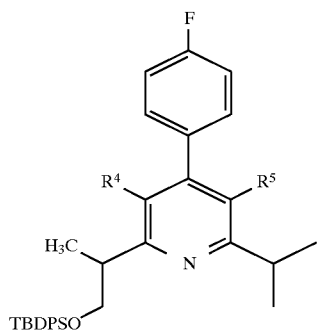

(VIII)

in which
$R^4$ and $R^5$ in each case represent the radical of the formula —$CO_2CH_3$ or —$CH_2OH$,
this is converted in a further step by a reaction with sodium hydride in inert solvents into the compounds of the formula (IX)

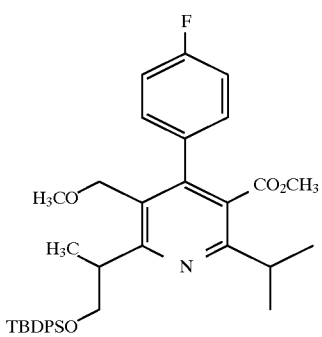

(IX)

and finally this is reduced with lithium aluminium hydride in inert solvents.

Suitable solvents for the individual steps are the solvent indicated above or acetonitrile, water or toluene.

Acetonitrile/water is preferred for the reaction of the compounds of the formula (VI) and toluene and tetrahydrofuran are preferred for the preparations of the compounds of the general formulae (VII) and (VIII).

With the exception of the reductions, the reactions are carried out in a temperature range from −75° C. to +50° C., preferably at room temperature.

The reactions are in general carried out at normal pressure, but it is also possible to work at reduced pressure or elevated pressure.

Suitable reducing agents for the reaction of the compounds of the general formula (VII) and the reaction of the compounds of the general formula (IX) are metal hydrides, such as, for example, lithium aluminium hydride, sodium cyanoborohydride, sodium aluminium hydride, diisobutylaluminium hydride or sodium bis-(2-methoxyethoxy) dihydroaluminate.

In the case of the compounds of the general formula (VII), diisobutylaluminium hydride is preferred and, in the case of the compounds of the general formula (IX), lithium aluminium hydride.

The reducing agent is in general employed in an amount from 4 mol to 10 mol, preferably from 4 mol to 5 mol, relative to 1 mol of the compounds of the general formulae (VII) and (VIII).

The reduction in general proceeds in a temperature range from −78° C. to +100° C., preferably from −78° C. to 0° C., particularly preferably at −78° C., in each case depending on the choice of the reducing agent.

The reduction in general proceeds at normal pressure, but it is also possible to work at elevated or reduced pressure.

The compounds of the general formula (II) in which $R^3$ represents the tert-butyldimethylsilyl radical can be prepared by a process in which methyl 6-[2-tert-butyldiphenylsilanyloxy-1-methyl-ethyl]-4-(4-fluorophenyl)-5-hydroxy-methyl-2-isopropylpyridine-3-carboxylate is reacted in dimethoxyethane with tert-butyldimethylsilyl chloride in the presence of imidazole and dimethylaminopyridine in a temperature range from 0° C. to +100° C., preferably at +50° C. under normal pressure.

The compounds of the formulae (VII), (VIII) and (IX) are new and can be prepared as described above.

The compound of the formula (VI) is new and can be prepared by a process in which 4-carbomethoxy-5-(4-fluorophenyl)-2-methyl-pent-4-en-3-one is reacted with methyl 5-tert-butyldiphenylsilanyloxy-4-methyl-3-oxopentanoate of the formula (X)

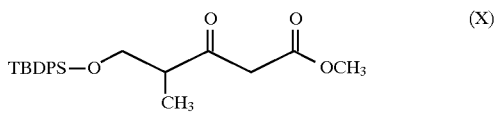
(X)

in methanol/sodium methoxide and ammonium acetate/glacial acetic acid at room temperature and normal pressure.

The compound of the formula (X) is new and can be prepared by a process in which methyl 3-tert-butyldiphenylsilanyloxy-2-methylpropionate of the formula (XI)

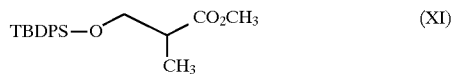
(XI)

is first converted by reaction with sodium hydroxide solution in tetrahydrofuran under reflux into the corresponding acid of the formula (XII)

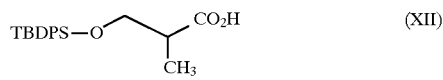
(XII)

this is then converted by reaction with N,N'-carbonyldiimidazole in tetrahydrofuran into the compound of the formula (XIII)

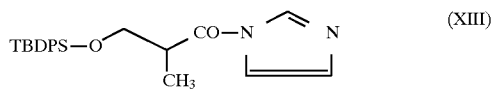
(XIII)

and in a last step this is reacted with potassium monomethylmalonate in acetonitrile, triethylamine and anhydrous magnesium chloride in a temperature range from 0° C. to +50° C., preferably from 0° C. to room temperature, and at normal pressure.

The compound of the formula (XI) is new and can be prepared by a process in which methyl 3-hydroxy-2-methylpropionate is reacted in dimethylformamide, tert-butyl-chlorodiphenylsilane, imidazole and 4-dimethylaminopyridine in a temperature range from −10° C. to +60° C., preferably from 0° C. to +45° C., and at normal pressure.

The compounds according to the invention have useful pharamcological properties which are superior in comparison to those of the prior art, in particular they are highly effective inhibitors of 3-hydroxy-3-methyl-glutaryl-coenzymeA (HMG-CoA) reductase and, as a result of this, inhibitors of cholesterol biosynthesis. They can therefore be employed for the treatment of hyperlipoproteinaemia or arteriosclerosis. The active compounds according to the invention bring about a lowering of the cholesterol content in the blood.

The pharmacological actions of the substances according to the invention were determined in the following test:
Biological test for HMGCoA reductase inhibitors Cholesterol is synthesized from acetate units in the mammalian body. In order to measure hepatic cholesterol biosynthesis in vivo, radiolabelled $^{14}C$-acetate was administered to the animals and the content of $^{14}C$-cholesterol in the liver was later determined.

The substances to be investigated were tested for inhibition of hepatic cholesterol biosynthesis in vivo on male Wistar rats having a body weight of between 140 and 160 g. For this purpose, the rats were weighed 18 hours before the oral administration of the substances, divided into groups of 6 animals (control group without substance loading 8 animals) and fasted. Directly before administration, the substances to be investigated were suspended in aqueous 0.75% strength tragacanth suspension using an Ultra-Turrax. The administration of the tragacanth suspension (control animals) or the substances suspended in tragacanth was carried out by means of a stomach tube. 2 hours after oral administration of substance, $^{14}C$-acetate (12.5 µgCi/animal) was injected intraperitoneally into the animals.

A further 2 hours later (4 hours after substance administration), the animals were sacrificed by cutting the throat and exsanguinated. The abdominal cavity was then opened and a liver sample of about 700 mg was taken to determine the $^{14}C$-cholesterol formed from 14C-acetate. The extraction of the cholesterol was carried out in a modified manner according to Duncan et al. (J. Chromatogr. 162 (1979) 281–292). The liver sample was homogenized in isopropanol in a glass potter. After shaking and subsequent centrifugation, the supernatant was mixed with alcoholic KOH and the cholesterol esters were hydrolysed. After hydrolysis, the total cholesterol was extracted by shaking with hexane and the supernatant was evaporated. The residue was taken up in isopropanol, transferred to scintillation tubes and made up with LSC cocktail. The $^{14}C$-cholesterol synthesized in the liver from $^{14}C$-acetate was measured in a liquid scintillation counter. The hepatic $^{14}C$-cholesterol content of the animals treated only with tragacanth served as a control. The inhibitory activity of the substances is indicated in % of the synthesized hepatic $^{14}C$-cholesterol content of the tragacanth control animals (=100%).

The present invention also includes pharmaceutical preparations which, in addition to inert, non-toxic, pharmaceutically suitable auxiliaries and excipients, contain one or more compounds of the general formula (I), or which consists of one or more active compounds of the formula (I), and processes for the production of these preparations.

The active compounds of the formula (I) should be present in these preparations in a concentration of 0.1 to 99.5% by weight, preferably of 0.5 to 95% by weight of the total mixture.

In addition to the active compounds of the formula (I), the pharmaceutical preparations can also contain other pharmaceutical active compounds.

The abovementioned pharmaceutical preparations can be prepared by known methods in a customary manner, for example with the auxiliaries or excipients.

In general, it has proved advantageous to administer the active compound(s) of the formula (I) in total amounts of approximately 0.1 µg/kg to approximately 100 µg/kg, preferably in total amounts of approximately 1 µg/kg to 50 µg/kg of body weight every 24 hours, if appropriate in the form of several individual doses, to achieve the desired result.

However, if appropriate it may be advantageous to depart from the amounts mentioned, namely depending on the type and the body weight of the subject treated, on individual behaviour towards the medicament, the nature and severity of the disorder, the manner of preparation and administration, and the time or interval at which administration takes place.

EXPERIMENTAL SECTION

Example I

Methyl (R)-3-tert-butyldiphenylsilanyloxy-2-methylpropionate

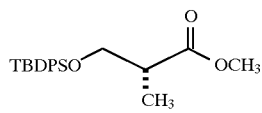

2667.0 g (22.60 mol) of methyl (R)-(−)-3-hydroxy-2-methylpropionate (EGA) are dissolved in 14 l of DMF p.a. in a 40 l stirring vessel. After addition of 6768.8 g (24.65 mol) of tert-butylchlorodiphenylsilane, 3376.4 g (49.65 mol) of imidazole and 10 g of 4-dimethylaminopyridine, the reaction temperature rises to 45° C. The reaction mixture is stirred with cooling at room temperature for 16 hours until conversion is complete. It is added to 75 l of water, washed twice with 20 l of ethyl acetate each time, and the combined organic phases are washed twice with 10 l of water each time, dried over sodium sulphate and concentrated in a rotary evaporator to give an oil.

Crude yield: 8928 g; 110% of theory; HPLC: 89.93%; TLC: $R_f$=0.78 (petroleum ether/ethyl acetate 9:1); $^1$H-NMR (200 MHz, $d_6$-DMSO, TMS): δ=0.98 (s, 9H, t-Bu); 1.10 (d, 3H, $CH_3$); 2.74 (m, 1H, CH); 3.64 (s, 3H, $OCH_3$); 3.78 (d, 2H, $OCH_2$); 7.47 (m, 6H, Ar); 7.61 (m, 4H, Ar) ppm.

Example II (R)-3-tert-Butyldiphenylsilanyloxy-2-methylpropionic acid

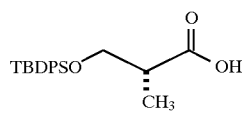

A solution of 4464 g ( 11.3 mol) of the compound from Example I (crude product) in 27.5 l of THF is heated under reflux (65° C. internal temperature) in a 40 l Stirring vessel for 46 hours with 5.65 l (11.3 mol) of 2 molar sodium hydroxide solution. THF is distilled off on a rotary evaporator, the residue is diluted with 5 l of water and 3 l of dichloromethane and the mixture is adjusted to pH 4 with 15% strength hydrochloric acid. The phases are separated, the aqueous phase is washed with 3 l of dichloromethane, and the combined organic phases are dried over sodium sulphate and concentrated to give an oil.

Crude yield: 3930 g; 100% of theory; HPLC: 67.17%; 14.21% silyl by-product; 16.81% starting material I; TLC: $R_f$=0.27 (petroleum ether/ethyl acetate 9:1); $^1$H-NMR (200 MHz, $d_6$-DMSO, TMS): δ=1.00 (s, 9H, t-Bu); 1.08 (d, 3H, $CH_3$); 2.60 (m, 1H, CH); 3.74 (m, 2H, $OCH_2$); 7.43 (m, 6H, Ar); 7.61 (m, 4H, Ar); 12.26 (s, 1H, COOH) ppm.

Example III (R)-3-tert-Butyldiphenylsilanyloxy-2-methylpropionic/acid imidazolide

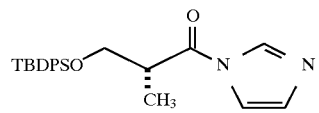

744.4 g (4.59 mol) of N,N'-carbonyldiimidazole are added at room temperature to a solution of 1927.5 g (3.77 mol) of the compound from Example II (67% strength) in 13 l of THF. The reaction mixture is stirred at room temperature for 1 hour and under reflux for 1 hour. After cooling to room temperature, the solution is employed in the next step without further purification.

Example IV

Methyl (R)-5-tert-butyldiphenylsilanyloxy-4-methyl-3-oxopentanoate 1258.3 g (8.06 mol) of potassium monomethyl malonate are suspended in 12.4 l of acetonitrile at 0° C. in a 40 l stirring vessel. 1124.5 ml (8.06 mol) of triethylamine and 847.1 g (8.92 mol) of anhydrous magnesium chloride are added and the mixture is stirred at room temperature for 5 hours. The reaction solution III and 112.4 ml (0.81 mol) of triethylamine are added in the course of 15 min, then the reaction mixture is stirred at room temperature for 16 hours. It is diluted with 20 l of ethyl acetate and adjusted to pH 4 using 15% strength hydrochloric acid. The organic phase is separated off, washed with 10 l of water and concentrated, the residue is taken up in 20 l of ethyl acetate and residual water is separated off. The organic phase is washed twice with 10 l of saturated sodium hydrogen carbonate solution each time until neutral, dried over sodium sulphate and concentrated in a rotary evaporator to give an oil.

Crude yield: 2012 g; 84.7% of theory; TPLC: 63.24%; 14.57% silyl secondary compound; 17.30% starting material I; TLC: $R_f$=0.56 (petroleum ether/ethyl acetate 9:1); $^1$H-NMR (200 MHz, $d_6$-DMSO, TMS): δ=1.00 (s, 9H, t-Bu and d, 3H, $CH_3$); 2.95 (m, 1H, CH); 3.65 (s, 3H, $OCH_3$); 3.72 (m, 4H, $CH_2$, $OCH_2$); 7.40 (m, 64H, Ar); 7.61 (m, 4H, Ar) ppm.

Example V (E/Z)-4-Carbomethoxy-5-(4-fluorophenyl)-2-methyl-pent-4-en-3-one

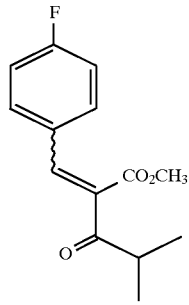

2094 g (14.54 mol) of methyl isobutyryl-acetate, 1442 g (11.6 mol) of 4-fluorobenzaldehyde, 46 ml of glacial acetic acid and 81 ml of piperidine are dissolved in 1.4 l of cyclohexane and the mixture is heated under reflux on a water separator. 240 ml of water separate in the course of 2.5 hours. Cyclohexane and glacial acetic acid are distilled off at 80 mbar, then the starting materials are distilled off at 2 mbar (bath temperature 120° C., head temperature 70° C.). The residue is treated at room temperature with 3 l of ethyl acetate, then the mixture is washed with sodium hydrogen carbonate, dried over sodium sulphate and concentrated to give an oil.

Crude yield: 2930 g; 61.14% of theory; HPLC: 31.51%; 61.14% E/Z; $^1$H-NMR (200 MHz, CDCl$_3$, TMS): δ=1.10 and 1.18 (2d, 6H, CH$_3$); 2.71 and 3.18 (2 sept., 1H, CH); 3.84 (2s, 3H, OCH$_3$); 7.07 (m, 2H, Ar); 7.40 (m, 2H, Ar); 7.58 and 7.75 (2s, 1H, olefinH) ppm.

By triturating with petroleum ether one diastereomer is obtained as a solid. Melting point: 56°–58° C. $^1$H-NMR (CDCl$_3$): δ=1.09 (d, 6H, CH$_3$); 2.71 (sept., 1H, CH); 3.84 (s, 3H, OCH$_3$); 7.07 (m, 2H, Ar); 7.40 (m, 2H, Ar); 7.75 (s, 1H, olefinH) ppm.

Example VI

Dimethyl 6-[2-(tert-butyldiphenylsilanyloxy-1(S)-methyl-ethyl]-4(R,S)-(4-fluorophenyl)-2-isopropyl-1,4-dihydro-pyridine-3,5-dicarboxylate

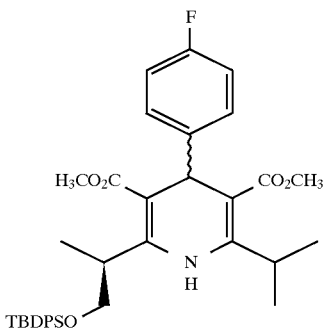

A solution of 560 g (2.01 mol) of the compound from Example V (crude product, 92% strength) and 1560 g (2.01 mol) of the compound from Example IV (crude product, 50% strength) in 3 l of methanol is cooled to 10° C. and treated in portions with 104 g (1.92 mol) of sodium methoxide, slight warming taking place. It is stirred at room temperature until the compound from Example V is converted completely (1.5 hours, HPLC checking). 480 g (6.25 mol) of ammonium acetate and 1.65 l of glacial acetic acid are then added and volatile fractions are distilled off over a distillation bridge at a bath temperature of 130°–140° C. (internal temperature 112° C., head temperature 105° C.). After 90 min, the Michael addition compound is completely reacted. 3 l of water are added at room temperature. The mixture is washed three times with 1.5 l of ethyl acetate each time, and the combined organic phases are washed with 2 l of water and 2 l of sodium hydrogen carbonate solution, dried over sodium sulphate and concentrated to give an oil.

Crude yield: 2015 g; 72.1% of theory based on 45.4% content; HPLC: 20.68% and 24.73% (2 diastereomers); $^1$H-NMR (CDCl$_3$): δ=0.94–1.35 (several d, 9H, CH$_3$); 1.13 (several s, 9H, t-Bu); 3.59, 3.63, 3.64, 3.67 (4s, 6H, 2 OCH$_3$); 3.73–4.30 (complex region, 4H, CH, OCH$_2$); 4.99 and 5.03 (2s, 1H, DHP-H); 6.80–7.78 (complex region, 14H, Ar) ppm.

FAB-MS: m/z=630(M+H)$^+$, 598, 534, 374, 322, 278, 213, 199, 197, 183, 135.

Example VII

Dimethyl 6-[2-(tert-butyldiphenylsilanyloxy-1(S)-methyl-ethyl]-4-(4-fluorophenyl)-2-isopropyl-pyridine-3,5-dicarboxylate

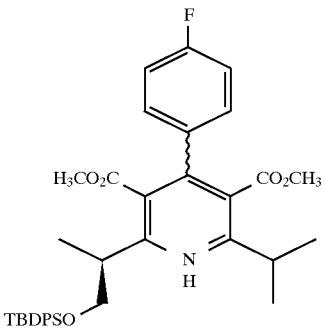

2015 g (about 1.45 mol) of the compound from Example VI are dissolved in 10 l of acetonitrile. 1698 g (3.1 mol) of ammonium cerium(IV) nitrate are added in portions at room temperature with stirring in the course of 10 min, the reaction mixture (suspension) warming to about 34° C. After 30 min, the reaction is complete (HPLC checking). The reaction mixture is stirred with 12 l of water and the acetonitrile is largely distilled off from the two-phase mixture on a rotary evaporator. Because of the danger of explosion, water should always be present during concentration. The aqueous residue is washed three times with 3 l of ethyl acetate each time, and the combined organic phases are washed with 3 l of 10% strength potassium iodide solution, with 3 l of sodium thiosulphate solution and with 5 l of water, dried over sodium sulphate and concentrated to give 1869 g of crude oil. The oil is chromatographed on 12 kg of silica gel 60 using about 90 l of petroleum ether/ethyl acetate 97:3.

Yield: 577.4 g of oil; 36.1% of theory; HPLC: 57.29%; A pure sample (oil) is obtained by repeated chromatography. $^1$H-NMR (200 MHz, CDCl$_3$, TMS): δ=0.96 (s, 9H, t-Bu); 1.25 (dd, 9H, CH$_3$); 3.07 (sept., 1H, CH(CH$_3$)$_2$); 3.30 (m, 1H, CH—CH$_2$); 3.48 (s, 3H, OCH$_3$); 3.57 (s, 3H, OCH$_3$); 3.70 and 4.05 (m, each 1H, CH$_2$O); 7.00–7.65 (m, 14H, Ar) ppm.

Examples VIII, IX and X

Methyl 6-[2-(tert-butyldiphenylsilanyloxy-1(S)-methyl-ethyl]-4-(4-fluorophenyl)-5-hydroxymethyl-2-isopropyl-pyridine-3-carboxylate

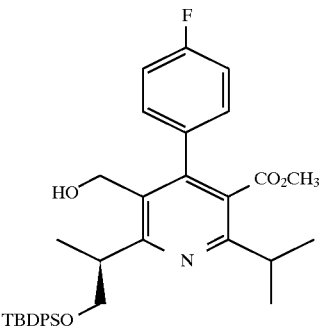

A solution of 561 g (0.51 mol) of the compound from Example VII (57.29% strength) in 1.7 l of toluene p.a. is cooled to −60° C. under an argon atmosphere. 1367 ml (2.05 mol) of a 1.5 molar diisobutylaluminium hydride solution in toluene are added dropwise to this solution in the course of 1.5 hours such that the internal temperature does not exceed −53° C. After addition is complete, the mixture is stirred at −60° C. for 30 min and at −30° C. for 16 hours until conversion is almost complete (TLC checking: petroleum ether/ethyl acetate 9:1). To hydrolyse the aluminium compounds, the reaction mixture is added to 8 l of 10% strength potassium hydroxide solution in the course of 20 min with stirring, stirring is continued for 15 min, and the aqueous phase is separated off, washed twice with 3 l of ethyl acetate each time and, to separate off flocks which make phase separation difficult, filtered with suction through kieselguhr. The combined organic phases are washed twice with 2 l of saturated sodium chloride solution each time, dried over sodium sulphate and concentrated on a rotary evaporator to give 525 g of crude oil. The crude oil is chromatographed on 13 kg of silica gel 60 using 100 l of petroleum ether/ethyl acetate 9:1 and 40 l of petroleum ether/ethyl acetate 8:2.

Yield: 124.9 g of oil; 43.2% of theory; HPLC: 99.0%; TLC: $R_f$=0.36 (petroleum ether/ethyl acetate 9:1); $^1$H-NMR (CDCl$_3$): δ=0.95 (s, 9H, t-Bu); 1.17 (d, 3H, CH$_3$); 1.25 (2d, 6H, CH$_3$); 3.05 (sept., 1H, CH); 3.45 (m, 1H, CH—CH$_2$); 3.57 (s, 3H, OCH$_3$); 3.62–3.77 (m 2H, CH$_2$O); 4.30 and 4.61 (m, je 1H, CH$_2$OSi); 7.02–7.65 (m, 14H, Ar) ppm. FAB-MS: m/z=600(M+H)$^+$, 542, 344, 326, 312, 199, 137, 135.

Furthermore, 42.3 g of starting material VII (HPLC: 99.26%; 13.2% of theory) and 244.3 g (HPLC: 34.95%; 29.5% of theory) of methyl 6-[2-(tert-butyldiphenylsilanyloxy-1(S)-methyl-ethyl]-4-(4-fluorophenyl)-3-hydroxymethyl-2-isopropyl-pyridine-5-carboxylate

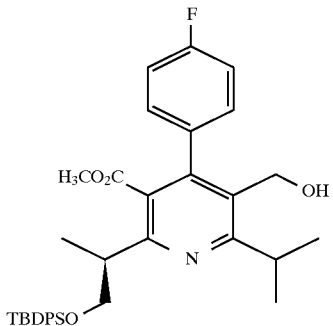

are isolated. A pure sample (oil) is obtained by repeated chromatography. $^1$H-NMR (200 MHz, CDCl$_3$, TMS): δ=0.95 (s, 9H, t-Bu); 1.23–1.35 (several d, 9H, CH$_3$); 3.22 (ddq, 1H, CH); 3.45 (s, 3H, OCH$_3$); 3.48 (sept., 1H, CH); 3.81 and 4.08 (m, 2H, OCH$_2$Si); 4.45 (2d, 2H, OCH$_2$); 7.02–7.67 (m, 14H, Ar) ppm.

In preliminary experiments, 6-[2-(tert-butyldiphenylsilanyloxy-1(S)-methyl-ethyl]-4-(4-fluorophenyl)-3,5-bishydroxymethyl-2-isopropyl-pyridine

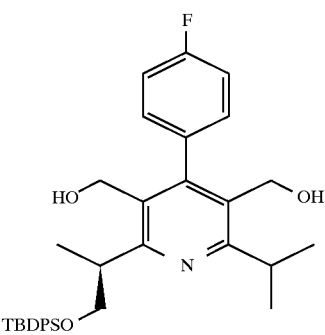

was obtained.

Melting point: 136° C.; TLC: $R_f$=0.12 (petroleum ether/ethyl acetate 9:1); $^1$H-NMR (200 MHz, CDCl$_3$, TMS): δ=0.91 (s, 9H, t-Bu); 1.20–1.35 (3d, 9H, CH$_3$); 1.38 (tr, 2H, OH); 3.28 (m, 1H); 3.49 (sept., 1H, CH); 3.67 (in, 1H); 3.80 (m, 2H); 4.13 and 4.38 (2m, 2H); 4.55 (m, 2H); 7.08–7.61 (complex region, 14H, Ar) ppm.

FAB-MS: m/z=572 (M+H)$^+$, 598, 534, 374, 322, 278, 213, 199, 197, 183, 135. ee=59.4% (HPLC)

Example XI

Methyl 6-[2-(tert-butyldiphenylsilanyloxy-1(S)-methyl-ethyl]-4-(4-fluorophenyl)-2-isopropyl-5-methoxymethyl-pyridine-3-carboxylate

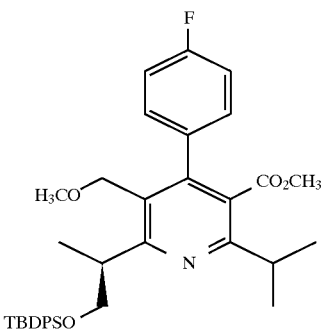

9.35 g (0.313 mol) of sodium hydride (80% strength) are suspended in 500 ml of absolute THF and the suspension is heated to boiling. A solution of 125 g (0.209 mol) of the compound from Example VIII in 300 ml of absolute THF is added dropwise under reflux. A solution of 35.5 g (0.25 mol) of methyl iodide in 100 ml of absolute THF is then also added dropwise under reflux. The mixture is then heated under reflux for a further 3 hours. After cooling to room temperature, 250 ml of water are added cautiously. The mixture is then extracted three times with 300 ml of ethyl acetate each time, and the combined organic phases are washed with saturated sodium chloride solution and dried over sodium sulphate. After stripping off the solvent in vacuo, the residue is chromatographed on silica gel (1 kg of silica gel 60, eluent petroleum ether/ethyl acetate 95:5).

Yield: 117.37 g; 91.74% of theory; TLC: $R_f$=0.55 (petroleum ether/ethyl acetate 9:1); $^1$H-NMR (CDCl$_3$): δ=0.95 (s, 9H, t-Bu); 1.22 (2d, 6H, CH$_3$); 1.30 (d, 3H,CH$_3$); 3.05 (sept., 1H, CH); 3.20 (s, 3H, OCH$_3$); 3.51 (s, 3H, OCH$_3$); 3.58 (m, 1H, CH—CH$_2$); 3.8–4.0 (m, 2H, CH$_2$O and 1H CH$_2$OSi); 4.45 (dd, 1H, CH$_2$OSi); 7.0–7.6 (m, 14H, Ar) ppm.

Example XII

6-[2-(tert-Butyldiphenylsilanyloxy-1(S)-methyl-ethyl]-4-(4-fluorophenyl)-2-isopropyl-5-methoxymethyl-pyridin-3-yl]methanol

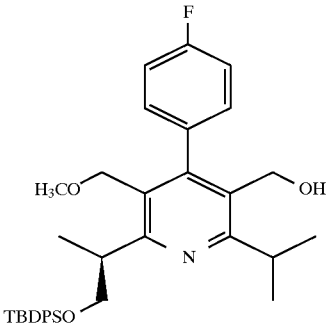

9 g (0.236 mol) of lithium aluminium hydride are suspended in 500 ml of absolute THF under argon and the mixture is heated to boiling. A solution of 72.3 g (0.118 mol) of the compound from Example XI in 300 ml of absolute THF is then added dropwise under reflux. The mixture is then heated under reflux for 1 hour. After cooling to room temperature, 80 ml of water are cautiously added dropwise. 80 ml of 10% strength potassium hydroxide solution are then added and the resulting precipitate is filtered off with suction. The precipitate is extracted by boiling three times with 300 ml of ether each time. The mother liquors are combined, dried over sodium sulphate and then concentrated in vacuo. The crude product thus obtained is employed in the next stage without further purification.

Yield: 69 g; 99% of theory; TLC: $R_f$=0.25 (petroleum ether/ethyl acetate 9:1); $^1$H-NMR (CDCl$_3$): δ=0.95 (s, 9H, t-Bu); 1.25 (2d, 6H, CH$_3$); 1.22 (d, 3H, CH$_3$); 3.15 (s, 3H, OCH$_3$); 3.42 (sept., 1H, CH); 3.53 (m, 1H, CH—CH$_3$); 3.8–4.0 (m, 3H, CH$_2$O and CH$_2$OSi); 4.35–4.45 (m, 3H, CH$_2$OH, CH$_2$OSi); 7.0–7.6 (m, 14H, Ar) ppm.

Example XIII

6-[2-(tert-Butyldiphenylsilanyloxy-1(S)-methyl-ethyl]-4-(4-fluorophenyl)-2-isopropyl-5-methoxymethyl-pyridine-3-carbaldehyde

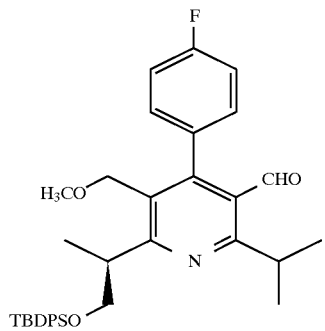

48.1 g (0.472 mol) of aluminium oxide and 101.7 g (0.472 mol) of pyridinium chlorochromate are added to a solution of 138 g (0.236 mol) of the compound from Example XII in 3.5 l of dichloromethane. After stirring at room temperature for 1 hour, the mixture is washed through a frit with 500 g of silica gel 60 and with sufficient dichloromethane. The filtrate is then concentrated in vacuo and dried.

Yield: 95.4 g; 69.3% of theory; TLC: $R_f$=0.59 (petroleum ether/ethyl acetate 9:1); $^1$H-NMR (CDCl$_3$): δ=0.9 (s, 9H, t-Bu); 1.22 (d, 6H, 2×CH$_3$); 1.30 (d, 3H, CH$_3$); 3.21 (s, 3H, OCH$_3$); 3.62 (m, 1H, CH); 3.8–4.0 (m, 2H CH$_2$O, 1H CH—CH$_2$, 1H CH$_2$OSi); 4.46 (dd, 1H, CH$_2$OSi); 7.0–7.7 (m, 14H, Ar); 9.78 (s, 1H, CHO) ppm.

Example XIV

Methyl (E)-7-{6-[2-(tert-butyldiphenylsilanyloxy)-1(S)-methyl-ethyl]-4-(4-fluorophenyl)-2-isopropyl-5-methoxymethyl-pyrid-3-yl}-(3R)-tert-butyldimethyl-silanyloxy-5-oxo-hept-6-enoate

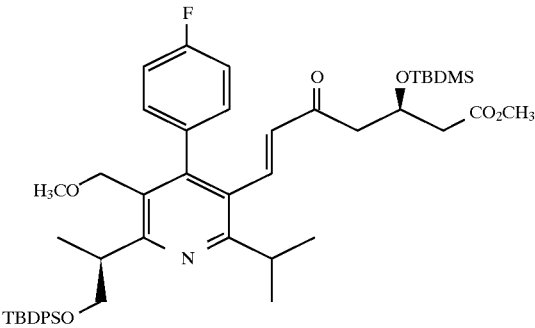

82.5 g (0.22 mol) of R-ketophosphonate (CH$_3$O)$_2$PO—CH$_2$—CO—CH$_2$CH(OTBDMS)—CH$_2$—CO$_2$CH$_3$, 29.6 g (0.214 mol) of potassium carbonate and 2.9 ml of water are dissolved in 635 ml of isopropanol and the mixture is stirred at room temperature for 1 hour. 95.4 g (0.16 mol) of the compound from Example XIII suspended in 150 ml of isopropanol are then added. After stirring at room temperature for 4 days (TLC checking), 500 ml of water are added and the mixture is then extracted three times by shaking with 500 ml of ethyl acetate. The combined ethyl acetate phases are washed with saturated sodium chloride solution, dried over sodium sulphate and concentrated in vacuo. The residue is chromatographed on silica gel (1 kg of silica gel 60, eluent petroleum ether/ethyl acetate 95:5).

Yield: 112.1 g; 81.6% of theory; TLC: $R_f$=0.32 (petroleum ether/ethyl acetate 9:1); $^1$-H-NMR (CDCl$_3$): −0.2 (s, 3H, CH$_3$Si); 0.3 (s, 3H, CH$_3$Si); 0.75 (s, 9H, t-Bu); 0.9 (s, 9H, t-Bu); 1.15–1.35 (m, 9H, 3×CH$_3$); 2.38 (m, 2H, CH$_2$); 2.56 (d, 2H CH$_2$); 3.12 (s, 3H, OCH$_3$); 3.23 (sept., 1H, CH); 3.52 (m, 1H, CH—CH$_2$); 3.61 (s, 3H, OCH$_3$); 3.75–3.95 (m, 2H CH$_2$O and 1H CH$_2$OSi); 4.38 (dd, 1H, CH$_2$OSi); 4.47 (m, 1H, CH$_2$ OSi); 5.85 (d, 1H =CH); 6.9–7.6 (m, 14H, Ar and 1H =CH) ppm.

Example XV

Methyl (E)-7-{4-(4-fluorophenyl)-6-[1(S)-hydroxymethyl-ethyl]-2-isopropyl-5-methoxymethyl-pyrid-3-yl}-(3R)-hydroxy-5-oxo-hept-6-enoate

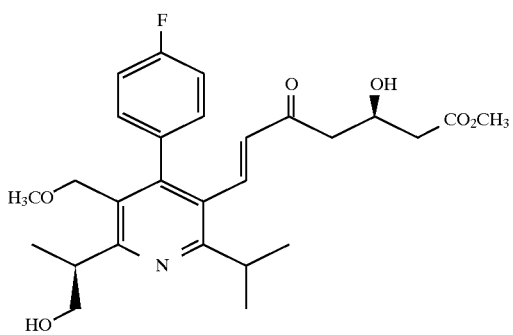

A solution of 112 g (0.133 mol) of the compound from Example XIV in 1170 ml of absolute methanol and 130 ml of 1 molar hydrochloric acid is stirred at room temperature for 4 days (TLC checking). 1000 ml of dichloromethane are then added and the mixture is extracted twice with 500 ml of saturated sodium hydrogen carbonate solution each time. The organic phase is dried with sodium sulphate and concentrated in vacuo. The residue is chromatographed on silica gel (1 kg of silica gel 60, eluent petroleum ether/ethyl acetate 1:1).

Yield: 59.2 g; 91% of theory; TLC: $R_f$=0.17 (petroleum ether/ethyl acetate 1:1); $^1$H-NMR (CDCl$_3$): δ=1.28 (2d, 6H, CH$_3$); 1.42 (d, 3H, CH$_3$); 2.48 (m, 2H, CH$_2$); 2.61 (m, 2H, CH$_2$); 3.20 (s, 3H, OCH$_3$); 3.28 (sept., 1H, CH); 3.32 (m, 2H, CH$_2$OH); 3.71 (s, 3H, OCH$_3$); 3.88 (m, 1H, CH—CH$_2$); 4.0–4.2 (m, 2H, CH$_2$O); 4.41 (m, 1H, CHOH); 5.90 (d, 1H =CH); 7.0–7.2 (m, 4H, Ar); 7.45 (d, 1H, =CH) ppm.

Example XVI

Methyl 6-[2-(tert-butyldiphenylsilanyloxy)-1(S)-methyl-ethyl]-5-tert-butyldimethyl-silanyloxymethyl-4-(4-fluorophenyl)-2-isopropyl-pyridine-3-carboxylate

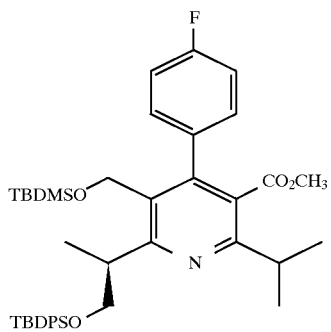

3 g (0.05 mol) of the compound from Example VIII are stirred at 50° C. overnight in 400 ml of dimethoxyethane with 16.6 g (0.11 mol) of tert-butyldimethylsilyl chloride, 15 g (0.22 mol) of imidazole and 1 g (8 mmol) of dimethylaminopyridine. After cooling, the mixture is diluted with 100 ml of diethyl ether and extracted with 200 ml of saturated sodium chloride solution. After drying with sodium sulphate, the organic phase is concentrated and the residue is chromatographed on silica gel (500 g of silica gel 60, eluent petroleum ether/ethyl acetate 95:5).

Yield: 35.57 g; 99.8% of theory; TLC: $R_f$=0.30 (petroleum ether/ethyl acetate 95:5); $^1$H-NMR (CDCl$_3$): δ=−0.3 (s, 3H); 0.1 (s, 3H); 0.87 and 0.92 (2s, 18H); 1.2–1.35 (3d, 9H); 3.0 (sept, 1H); 3.51 (s, 3H); 3.6–3.75 (m, 1H); 3.8–4.25 (m, 4H); 4.78 (dd, 1H); 6.95–7.65 (m, 14H) ppm.

Example XVII

6-[2-(tert-Butyldiphenylsilanyloxy)-1(S)-methyl-ethyl]-5-tert-butyldimethylsilanyloxy-methyl-4-(4-fluorophenyl)-3-hydroxymethyl-2-isopropylpyridine

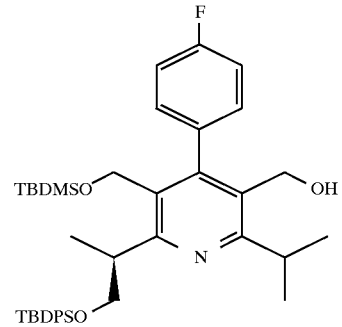

3.79 g (0.1 mol) of lithium aluminium hydride suspended in 250 ml of absolute THF are heated to boiling under argon. A solution of 35.57 g (0.05 mol) of the compound from Example XVI in 150 ml of absolute THF is added dropwise under reflux. The mixture is then heated under reflux for 1 hour. After cooling to room temperature, 30 ml of water are cautiously added dropwise. 30 ml of 10% strength potassium hydroxide solution are then added and the resulting precipitate is filtered off with suction. The precipitate is extracted by boiling three times with 100 ml of diethyl ether each time. The mother liquors are combined, dried over sodium sulphate and then concentrated in vacuo. The crude product thus obtained is employed in the next stage without further purification.

Yield: 33.49 g; 98% of theory; TLC: $R_f$=0.24 (petroleum ether:ethyl acetate 9:1); $^1$H-NMR (CDCl$_3$): δ=−0.8 (s, 3H); −0.2 (s, 3H); 0.85 and 0.92 (2s, 18H); 1.2–1.35 (3d, 9H); 3.42 (sept, 1H); 3.6–4.15 (m, 6H); 4.4 (AB, 2H); 4.72 (d, 1H); 6.95–7.65 (m, 14H) ppm.

Example XVIII

6-[2-(tert-Butyldiphenylsilanyloxy)-1(S)-methyl-ethyl]-5-tert-butyldimethyl-silanyloxymethyl-4-(4-fluorophenyl)-2-isopropyl-pyridine-3-carbaldehyde

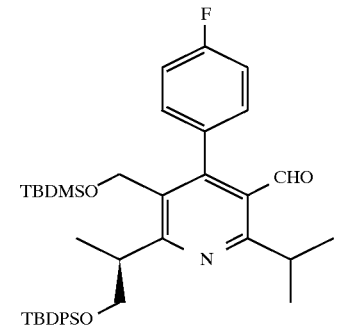

9.97 g of aluminium oxide and 21.08 g (0.098 mol) of pyridinium chlorochromate are added to a solution of 33.49 g (0.1 mol) of the compound from Example XVII in 600 ml of dichloromethane. After stirring at room temperature for 1 hour, the mixture is filtered through a frit with silica gel (100 g of silica gel 60) and washed with sufficient dichloromethane. The filtrate is then concentrated in vacuo and dried.

Yield: 26.56 g; 79.5% of theory; TLC: $R_f$=0.20 (petroleum ether:ethyl acetate 9:1); $^1$H-NMR (CDCl$_3$)

δ=–0.5 (s, 3H); –0.1 (s, 3H); 0.87 and 0.89 (2s, 18H), 1.2–1.3 (3d, 9H); 3.65–4.2 (m, 2H, CH$_2$O; 1H, CHCH$_2$; 1H, CH$_2$OSi); 4.78 (dd, 1H); 7.05–7.65 (m, 14H); 9.78 (s, 1H) ppm.

Example XIX

Methyl (E)-7-{6-[2-(tert-butyldiphenylsilanyloxy)-1(S)-methyl-ethyl]-5-tert-butyldimethylsilanyl-oxy-methyl-4-(4-fluorophenyl)-2-isopropyl-pyridin-3-yl}-(3R)-tert-butyldimethylsilanyloxy-5-oxo-hept-6-enoate

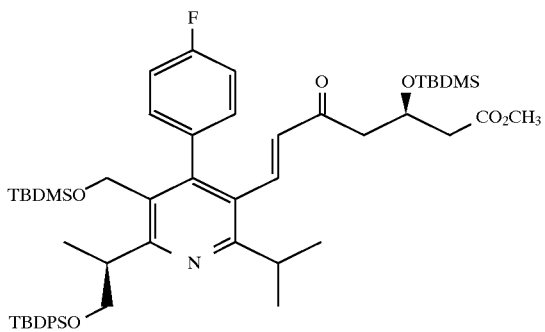

2.4 g (6.38 mmol) of R-ketophosphonate (CH$_3$O)$_2$PO—CH$_2$CH(OTBDMS)—CH$_2$—CO$_2$CH$_3$, 0.875 g (6.33 mmol) of potassium carbonate and 85.8 ml of H$_2$O are dissolved in 18.8 ml of isopropanol and the solution is stirred at room temperature for 1 hour. 3.3 g (4.83 mmol) of the compound from Example XVIII dissolved in 18.8 ml of isopropanol are then added. After stirring at room temperature for 5 days (TLC checking), 100 ml of water are added and the mixture is then extracted three times by shaking with 100 ml of ethyl acetate. The combined organic phases are washed with sodium chloride solution, dried with sodium sulphate and concentrated in vacuo. The residue is chromatographed on silica gel (500 g of silica gel 60, eluent petroleum ether:ethyl acetate 95:5)

Yield: 3.6 g; 79.4% of theory; TLC: R$_f$=0.31 (petroleum ether:ethyl acetate 9:1); $^1$H-NMR (CDCl$_3$) δ=–0.5, –0.1 and 0.2 (3s, 12H); 0.8, 0.87 and 0.9 (3s, 27H); 1.15–1.35 (3d, 9H); 2.42 (m, 2H); 2.6 (d, 2H); 3.28 (sept, 1H); 3.65 (s, 3H); 3.8–4.2 (m 3H); 4.52 (m, 1H); 4.73 (d, 1H); 5.90 (d, 1H); 6.9–7.65 (m, 15H) ppm.

Example XX

Methyl (E)-7-{6-[1(S)-hydroxy- ethyl-ethyl]-5-hydroxymethyl-4-(4-fluoro-phenyl)-2-isopropyl-pyridin-3-yl}-(3R)-hydroxy-5-oxo-hept-6-enoate

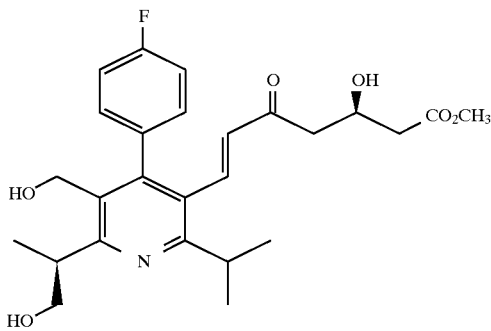

A solution of 3.6 g (3.8 mmol) of the compound from Example XIX in 63 ml of methanol and 7 ml of 1 molar hydrochloric acid is stirred at room temperature for 5 days. 100 ml of dichloromethane are then added and the mixture is extracted twice with 100 ml of saturated sodium hydrogen carbonate solution each time. The organic phase is dried with sodium sulphate and concentrated in vacuo. The residue is chromatographed on silica gel (500 g of silica gel 60, eluent ethyl acetate:petroleum ether 6:4).

Yield: 1.4 g; 77.9% of theory; TLC: R$_f$=0.15 (ethyl acetate:petroleum ether 6:4); $^1$H-NMR (CDCl$_3$) δ=1.2–1.45 (3d, 9H); 2.48 (d, 2H); 2.6 (m, 2H); 3.2–3.6 (m, 3H); 3.7 (s, 3H); 3.8–4.6 (m, 4H); 5.92 (d, 1H); 7.0–7.4 (m, 5H) ppm.

Preparation examples:

Example 1

Methyl (E)-7-{4-(4-fluorophenyl)-6-[1(S)-hydroxymethyl-ethyl]-2-isopropyl-5-methoxymethyl-pyridin-3-yl}-3(R),5(S)-dihydroxy-hept-6-enoate

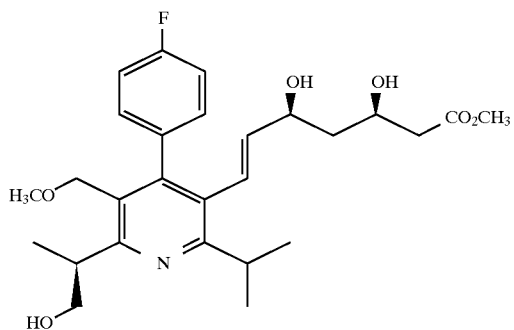

600 ml of absolute THF, 240 ml of absolute methanol and 243.2 ml (0.24 mol) of a 1 molar triethylborane solution in THF are stirred at room temperature for I hour. After cooling to –75° C. (internal temperature, acetone/dry-ice cooling), 59.2 g (0.12 mol) of the compound from Example XV dissolved in 150 ml of absolute THF are added. After 30 min at –75° C., 6.9 g (0.18 mol) of sodium borohydride are added in portions and the mixture is then stirred at –75° C. for a further 3 hours. The cooling bath is removed and 100 ml of saturated ammonium chloride solution are added dropwise at 0° C. 700 ml of water and 500 ml of ethyl acetate are then added. The aqueous phase is separated off and washed twice with 200 ml of ethyl acetate each time. The combined organic phases are washed with 400 ml of saturated sodium chloride solution, dried over sodium sulphate and then concentrated in vacuo. The residue is dissolved in 500 ml of methanol and concentrated on a rotary evaporator again 6 times and then chromatographed on silica gel (1.3 kg of silica gel 60, eluent petroleum ether/ethyl acetate 1:1). The product-containing fractions are concentrated. 50.5 g of crude product are obtained, which are again chromatographed on silica gel.

Yield: 33.9 g; 57.8% of theory; de=59% (HPLC); TLC: R$_f$=0.14 (petroleum ether/ethyl acetate 1:1); $^1$H-NMR (CDCl$_3$): δ=1.25 (2d, 6H, CH$_3$); 1.40 (m, 2H, —CH$_2$—); 1.43 (d, 3H, CH$_3$); 2.41 (m, 2H, —CH$_2$—); 3.18 (s, 3H, OCH$_3$); 3.2–3.4 (m, 2H, CH and CH—CH$_2$); 3.71 (s, 3H, OCH$_3$); 3.85 (m, 2H, CH$_2$—OH); 4.0–4.2 (m, 3H, CH$_2$O and CHO); 4.32 (m, 1H, CHO); 5.28 (dd, 1H, =CH); 6.31 (d, 1H, =CH); 7.0–7.2 (m, 4H, Ar) ppm.

Separation of the diastereomers of the compound from Example 1 (de=59%) by preparative HPLC 30 g of the compound from Example 1 are dissolved in 160 ml of ethanol p.a. (Merck) and diluted with 640 ml of n-heptane (LiChrosolv, Merck). By means of an autoinjector, 940 injections of 0.8 ml (30 mg) are made on the HPLC column every 15 min and 13 fractions are collected with the aid of a fraction collector by means of a peak/time control. After checking the purity of these fractions by means of HPLC, the fractions 1–6 (peak 1, diastereomer 1A), 7+8 (mixture A+B) and 9–13 (peak 2, diastereomer 1B) are each combined. The solvent is distilled off in vacuo on a rotary evaporator. The mixed fractions are again separated in an analogous manner.

Yield: 16.9 g of 1A (de=99.2%), 76% of theory based on 1; 4 g of 1B (de=77.8%), 70% of theory based on 1.

Preparative HPLC parameters

| | |
|---|---|
| Apparatus: | High-pressure pumps Models 305 and 306 (Gilson) Fraction collector Model 201 (Gilson) Autoinjector Model 231 XL (Gilson) Detector Model SP 100 (Spectra Physics) Recorder Model 320 D (Servogor) |
| Column: | Length: 250 mm; internal diameter: 20 mm; temperature: 40° C. |
| Stationary phase: | Chiralpak AS, No. 068-702-40914 (Daicel Chemical Ind.) |
| Eluent: | n-Heptane (LiChrosolv, Merck) 95%, ethanol (p.a., Merck) 5% |
| Flow rate: | 10 ml/min |
| Detection: | UV, 230 nm |
| Pressure: | $2 \times 10^6$ Pa |

Example 2

Sodium (E)-7-{4-(4-fluorophenyl)-6-[1(S)-hydroxymethyl-ethyl]-2-isopropyl-5-methoxymethyl-pyridin-3-yl}-3(R),5(S)-dihydroxy-hept-6-enoate

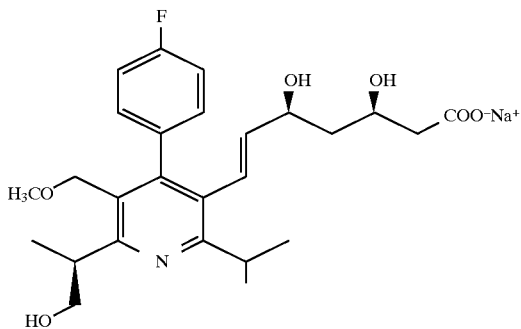

10.6 g (21.68 mmol) of the compound 1A are dissolved in 150 ml of THF. 238.5 ml of 0.1 molar sodium hydroxide solution are added at room temperature. After 1 hour at room temperature, the THF is removed on a rotary evaporator and the aqueous residue is freeze-dried.

Yield: 10.7 g; 99.3% of theory

Example 3

Methyl (E)-7-{6-[1(S)-hydroxy-methyl-ethyl]-5-hydroxymethyl-4-(4-fluorophenyl)-2-isopropyl-pyridin-3-yl}-(3R),5(S)-dihydroxy-hept-6-enoate

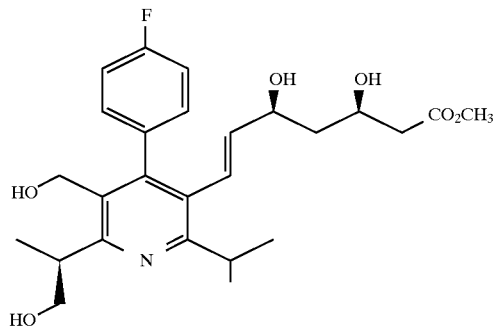

24 ml of absolute THF, 6 ml of absolute methanol and 5.9 ml (5.92 mmol) of a 1 molar triethylborane solution in THF are stirred at room temperature for 1 hour. After cooling to −75° C., 1.4 g (2.96 mmol) of the compound from Example XX dissolved in 20 ml of absolute THF are added. After 30 min at −75° C., 168 mg (4.44 mmol) of sodium borohydride are added in portions and the mixture is then stirred at −75° C. again for 3 hours. The cooling bath is removed and 100 ml of saturated ammonium chloride solution are added dropwise at 0° C. 100 ml of water and 100 ml of ethyl acetate are then added. The aqueous phase is separated off and washed twice with 100 ml of ethyl acetate each time, dried with sodium sulphate and then concentrated in vacuo. The residue is dissolved four times in 100 ml of methanol and again concentrated on a rotary evaporator and then chromatographed on silica gel (500 g of silica gel 60, eluent ethyl acetate petroleum ether 6:4).

Yield: 1.16 g; 82.5% of theory. (de=59%, HPLC); TLC: $R_f$=0.33 (ethyl acetate/petroleum ether 7:3); $^1$H-NMR (CDCl$_3$) δ=1.15–1.3 and 1.4 (3d, 9H); 2.42 (m, 2H); 3.1 (m, 1H); 3.2–3.65 (m, 3H); 3.71 (s, 3H); 3.8–4.55 (m, 6H); 5.78 (dd, 1H); 6.3 (d, 1H); 7.25 (m, 4H) ppm.

The pure diastereomer is obtained by preparative HPLC as described in Example 1.

Example 4

Sodium (E)-7-{6-[1(S)-hydroxy-methyl-ethyl]-5-hydroxymethyl-4-(4-fluorophenyl)-2-isopropyl-pyridin-3-yl}-(3R),5(S)-dihydroxy-hept-6-enoate

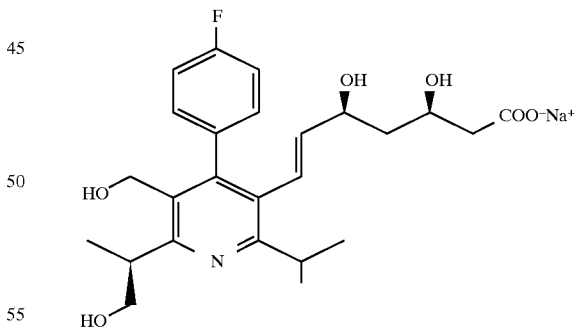

504 mg (1.06 mmol) of the compound from Example 3 are dissolved in 10 ml of THF. 10.6 ml of 0.1 molar sodium hydroxide solution are added at room temperature. After 1 hour at room temperature, the THF is stripped off on a rotary evaporator and the aqueous residue is freeze-dried.

Yield: 511 mg; 99.7% of theory. de>99% (HPLC); $^1$H-NMR (CD$_3$OD): δ=1.23, 1.25, 1.36 (3d, 9H); 1.26 (ddd, 1H); 1.51 (ddd, 1H); 2.17 (dd, 1H); 2.26 (dd, 1H); 3.45 (sept. 1H); 3.50 (m, 1H); 3.75 (m, 1H); 3.87 (m, 2H); 4.18 (m, 1H); 4.33 (m, 2H); 5.34 (dd, 1H); 6.29 (dd, 1H); 7.11–7.22 (m, 4H) ppm.

We claim:
1. A 6-(hydroxymethyl-ethyl)pyridine of the formula (I)

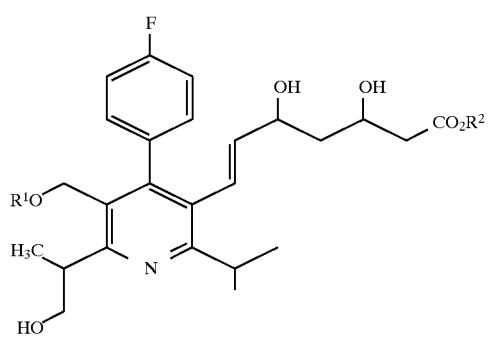

in which
R[1] represents hydrogen or methyl, and
R[2] represents hydrogen or methyl,
or a physiologically acceptable salt thereof.

2. A 6-(hydroxymethyl-ethyl)pyridine of the formula (I) according to claim 1, which has the erythro configuration or a physiologically acceptable salt thereof.

3. A 6-(hydroxymethyl-ethyl)pyridine of the formula (I) according to claim 1, which is a 1S or 1R enantiomer of (3R, 5S)-dihydroxyheptenoic acid in the erythro(E) configuration, or a physiologically acceptable salt thereof.

4. A process for the preparation of a 6-(hydroxymethyl-ethyl)pyridine according to claim 1, comprising
a) oxidizing a compound of the formula (II)

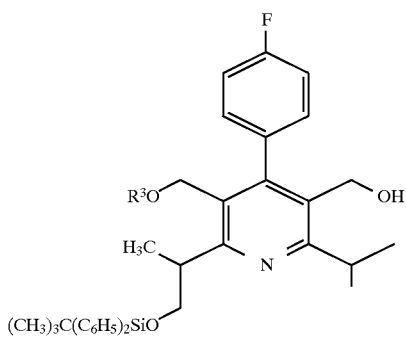

in which
R[3] represents methyl or the radical —Si(CH$_3$)$_2$C(CH$_3$)$_3$ (TBDMS),
with aluminum oxide and pyridinium chlorochromate in an inert solvent to give the aldehyde of the formula (III)

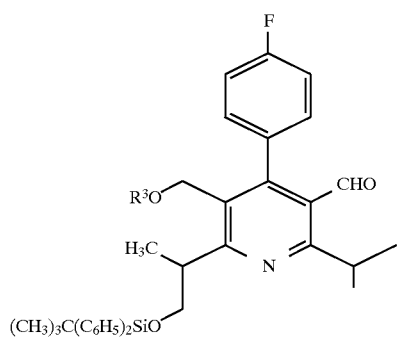

in which
R[3] has the meaning indicated above,
b) reacting the aldehyde of formula (III) with the keto-phosphonate (CH$_3$O)$_2$PO—CH$_2$—CO—CH$_2$—CH(OSi(CH$_3$)$_2$)C(CH$_3$)$_3$)—CH$_2$—CO$_2$CH$_3$ in the presence of a base and solvent to give the compound of the formula (IV)

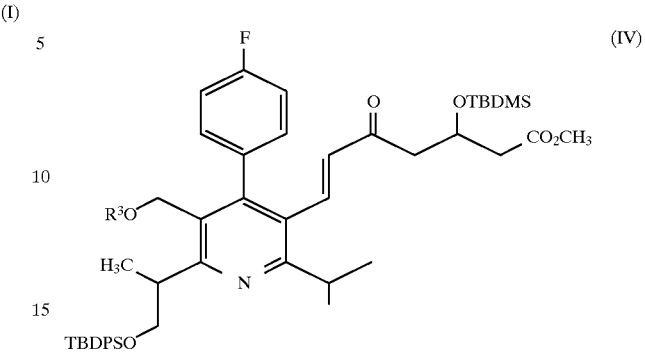

in which
TBDPS=(CH$_3$)$_3$C(C$_6$H$_5$)$_2$Si, and
R[3] has the meaning indicated above,
c) removing the hydroxyl protective group TBDPS and TBDMS to give the compound of the formula (V)

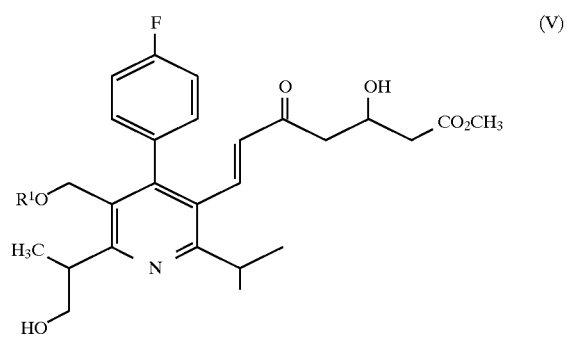

in which
R[1] has the meaning indicated in claim 1, and
d) reducing the keto group

of the compound of formula (V) in an inert solvent using sodium borohydride/triethylborane, and
e) optionally hydrolyzing the ester group (—CO$_2$CH$_3$) of the compound of formula (V).

5. The process according to claim 4, wherein e) gives a mixture of diastereomers, which are separated by chromatography or crystallization and converted into an enantiomerically pure compound.

6. A pharmaceutical composition comprising a 6-(hydroxymethyl-ethyl)pyridine of the formula (I) according to claim 1 or a physiologically acceptable salt thereof and a pharmaceutically acceptable carrier.

7. A method of treating a disorder arising from cholesterol biosynthesis comprising administering to a patient in need thereof an amount of a 6-(hydroxymethyl-ethyl)pyridine of the formula (I) according to claim 1 or a physiologically acceptable salt thereof, said amount being effective to inhibit 3-hydroxy-3-methyl-glutaryl-coenzyme A (HMG-CoA) reductase.

8. The method according to claim 6, wherein the disorder is hyperlipoproteinaemia.

9. The method according to claim 6, wherein the disorder is arteriosclerosis.

* * * * *